United States Patent [19]

Koch et al.

[11] Patent Number: 5,578,272

[45] Date of Patent: Nov. 26, 1996

[54] REAGENT KIT AND ANALYZER

[75] Inventors: Bruno Koch, Cham; Gottlieb Schacher, Ebikon, both of Switzerland

[73] Assignee: Hoffmann-La Roche Inc., Nutley, N.J.

[21] Appl. No.: 265,608

[22] Filed: Jun. 24, 1994

Related U.S. Application Data

[63] Continuation of Ser. No. 40,044, Mar. 30, 1993, abandoned.

[30] Foreign Application Priority Data

Apr. 9, 1992 [CH] Switzerland .............................. 1165/92

[51] Int. Cl.$^6$ ........................................................ B01L 3/00
[52] U.S. Cl. .............................................. 422/102; 422/104
[58] Field of Search ............................... 422/102, 61, 64, 422/65, 104, 100; 206/569

[56] References Cited

U.S. PATENT DOCUMENTS

| | | |
|---|---|---|
| 3,590,889 | 7/1971 | Vannus ................................. 422/100 |
| 3,897,216 | 7/1975 | Jones . |
| 3,917,455 | 11/1975 | Bak et al. . |
| 3,994,594 | 11/1976 | Sandrock et al. . |
| 4,168,955 | 9/1979 | Allington . |
| 4,338,279 | 7/1982 | Orimo et al. . |
| 4,366,119 | 12/1982 | Takeuchi ............................... 422/100 |
| 4,391,780 | 7/1983 | Boris . |
| 4,455,280 | 6/1984 | Shinohana et al. .................. 422/100 |
| 4,483,927 | 11/1984 | Takekawa ............................. 422/100 |
| 4,539,296 | 9/1985 | Manabe ................................... 436/47 |
| 4,608,231 | 8/1986 | Willy et al. . |
| 4,609,017 | 9/1986 | Coulter et al. . |
| 4,751,186 | 6/1988 | Busch et al. . |
| 4,847,050 | 7/1989 | Jenkins et al. . |
| 4,925,630 | 5/1990 | Grunwald . |
| 4,935,274 | 6/1990 | DeBenedictis et al. . |
| 4,970,053 | 11/1990 | Fechtner . |
| 5,005,721 | 4/1991 | Jordan . |
| 5,031,797 | 7/1991 | Boris et al. . |
| 5,035,861 | 7/1991 | Grandone . |
| 5,084,242 | 1/1992 | Sakuma et al. ...................... 422/100 |
| 5,128,105 | 7/1992 | Berthold et al. . |

FOREIGN PATENT DOCUMENTS

| | | |
|---|---|---|
| 674288 | 6/1966 | Belgium . |
| 192968 | 1/1986 | European Pat. Off. . |
| 223002 | 9/1986 | European Pat. Off. . |
| 252471 | 1/1988 | European Pat. Off. . |
| 3016605 | 11/1981 | Germany . |
| 55-141067 | 9/1980 | Japan . |
| 2-59672 | 2/1990 | Japan . |
| 80/00690 | 4/1980 | WIPO . |

OTHER PUBLICATIONS

Fumio et al., Patent Abstract of Japan, vol. 016, No. 251 (P–1366)8 (1992).
Pat. Abstract of Japan, vol. 12, No. 48 (P–666)13, (Feb./88) of Japanese Patent No. JP6219556.
Pat. Abstract of Japan, vol. 10, No. 264 (P–495)2320, (Sep./86) of Japanese Patent No. JP61088159.
Derwent Abstract No. 83704 D/46 of German Patent No. DE30 16 605 (May 1986).

*Primary Examiner*—Jill Warden
*Assistant Examiner*—Jan M. Ludlow
*Attorney, Agent, or Firm*—George W. Johnston; Robert A. Silverman

[57] ABSTRACT

A reagent kit having at least one container holding a reagent, and an analytical apparatus in which the reagent kit can be used. For the purpose of fully automatic processing of the reagent kit in an analytical apparatus, the reagent kit is characterized in that it is substantially a cuboid casing having a bottom, side walls and a removable lid and containers disposed in the casing, the lid having openings through which the contents of the reagent containers are accessible for automatic pipetting operations, each reagent container being closed by a closure, said closure being apt to be perforated by the needle of the pipetting device of an analytical apparatus, said closure being also apt to reclose the perforation after removal of the pipetting needle.

5 Claims, 7 Drawing Sheets

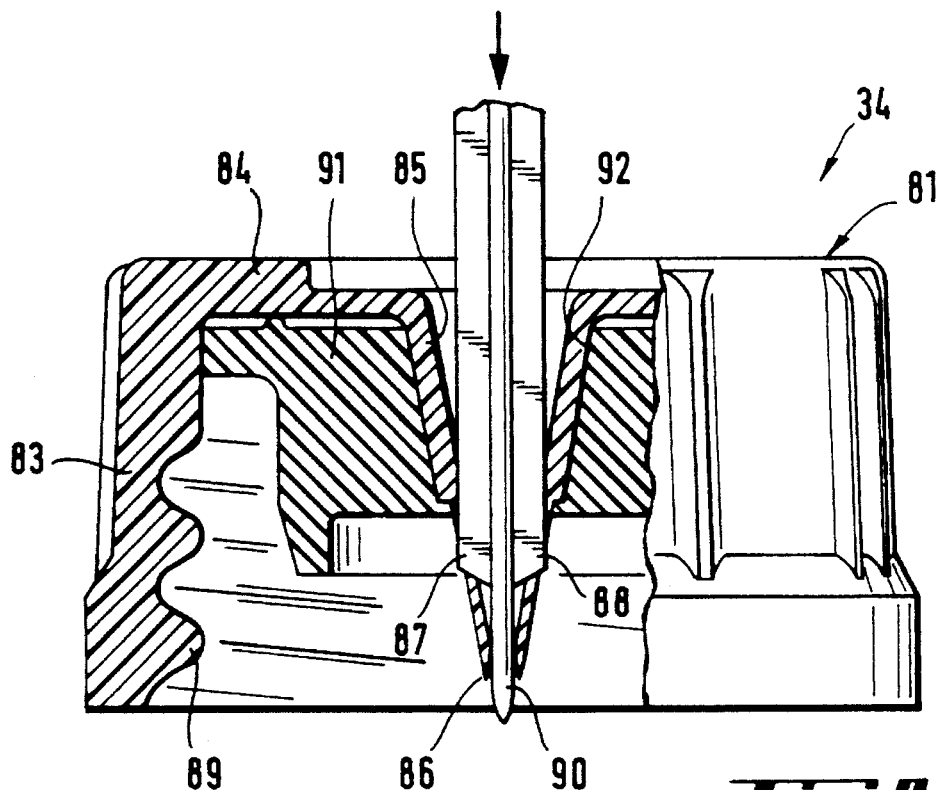
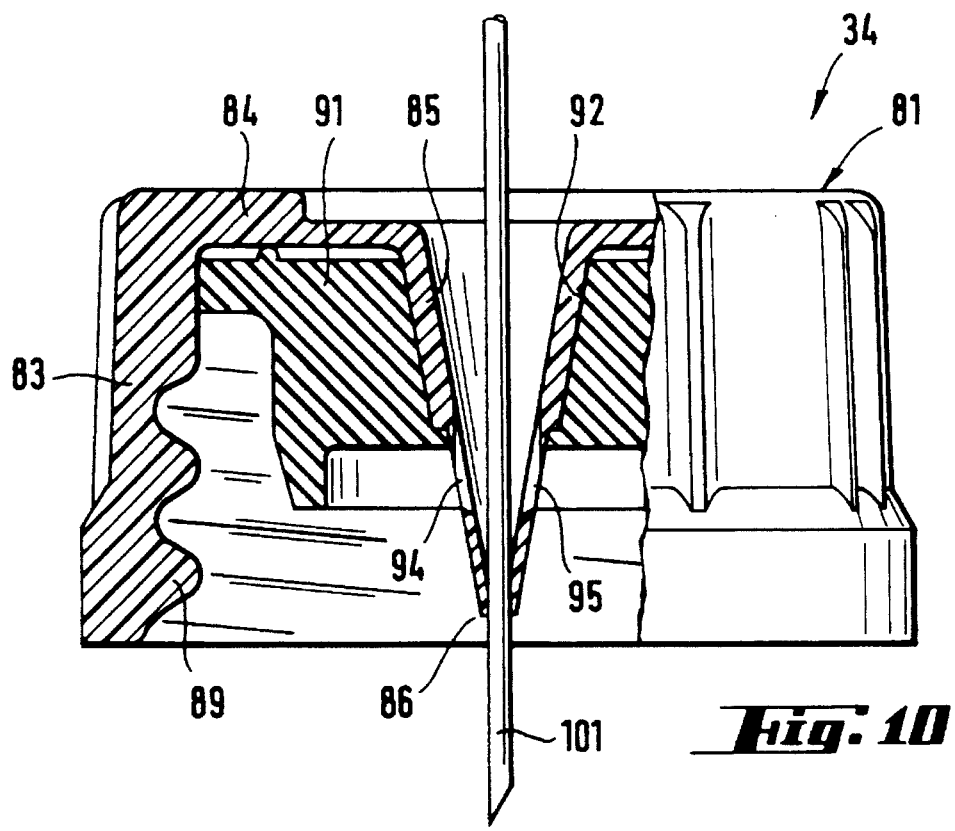

5,578,272

REAGENT KIT AND ANALYZER

This is a continuation of application Ser. No. 08/040,044 filed Mar. 30, 1993, now abandoned.

BACKGROUND OF THE INVENTION

1. Field of the Invention

The invention relates to a reagent kit for use in an automatic analytical apparatus. The invention also relates to an automatic analytical apparatus capable of holding a number of similar reagent kits.

2. Background Description

In automatic analytical apparatuses, it is desirable to process reagent kits which hold reagent containers completely automatically. Before being first used in the apparatus and between pipetting operations, the reagent containers also should be kept closed by a closure to avoid loss of reagent or shortening the useful life of the reagents.

In automatic analytical apparatuses in which there are a number of containers holding different reagents and a number of reaction vessels holding different specimens, it is also desirable for the pipetting device to have free access (random access) to any reagent container or to any reaction vessel.

The aim of the invention is to provide a reagent kit and an analytical apparatus for achieving the aforementioned aims.

SUMMARY OF THE INVENTION

According to an aspect of the invention, a reagent kit substantially comprises a cuboid casing having a bottom, side walls and a removable lid and containers disposed in the casing. The lid contains openings through which the contents of the reagent containers are accessible for automatic pipetting operations. Each reagent container is closed by a closure, and the closure preferably is apt to be perforated by a needle of a pipetting device of an analytical apparatus. The closure also preferably recloses and seals the perforation after removal of the pipetting needle.

The main advantage of the inventive reagent kit is that it makes it possible to attain the above mentioned desirable properties of closed reagent containers and random access, at a relatively low cost.

In a preferred embodiment of the reagent kit, the upper part of the casing has web means for gripping by a gripper belonging to a conveyor of the analytical apparatus. This facilitates automatic transport of the kit.

In a preferred embodiment of the reagent kit, one side wail of the casing bears a machine-readable label. This facilitates identification and automatic processing of the kit.

In another preferred embodiment of the reagent kit, the lid has pre-weakened or pre-punched portions which then can be opened by a spike. This enables marking of kits as used (previously analyzed) kits by punching such prepunched portions.

In another preferred embodiment of the reagent kit, the base and the cover of the casing have facing or oppositely opposed openings for circulating air through the casing and around the reagent containers therein. This makes it possible to maintain the reagents in the kit at the desired temperature by control of the temperature of the air flowing through the kit.

According to another aspect of the invention, an analytical apparatus contains an input station for inserting new reagent kits, and an output station for delivering used reagent kits or reagent kits which are not apt to be used in the analyzer. It also has a carrier plate on which the reagent kits in the analytical apparatus are arranged in a matrix. Conveyor means convey the reagent kits from the input station to the carrier plate or from the carrier plate to the output station and optionally to other positions inside the analytical apparatus. An automatic pipetting device carries out pipetting operations as required in the analytical apparatus. These pipetting operations include removal of predetermined volumes of reagent from the reagent containers and transfer of the volumes to reaction vessels. Each reaction vessel contains a specimen for examination and each reagent container is closed by a closure which can be perforated by a needle of the pipetting device.

The analytical apparatus according to the invention can be used for completely automatic processing of reagent kits. This reduces the need for labor in handling the analytical apparatus and also increases the reliability when performing a large number of different tests requiring a correspondingly large number of different reagents or combinations thereof.

A preferred embodiment of the analytical apparatus according to the invention comprises means for checking whether the reagent kits in the analytical apparatus are intact and acceptable for analysis. This prevents reagent kits which have already been used or consumed or otherwise unsatisfactory from being received in the analytical apparatus.

Another preferred embodiment of the analytical apparatus according to the invention contains a processing station in which a reagent kit can be disposed therein and pivoted. This, for example, allows complete dissolution of a reagent originally present in a container in freeze-dried form, in granulate form or in the form of a dry powder.

Another preferred embodiment of the analytical apparatus according; to the invention contains a reader for reading machine-readable information carried by a label disposed on each reagent kit. This is a method of automatically acquiring the relevant data of the reagent kit.

BRIEF DESCRIPTION OF THE DRAWINGS

An embodiment of the invention will now be described with reference to the accompanying drawings, in which:

FIG. 9 is a view partly in cross-section of the closure 34 in FIG. 6 and a spike 90 inserted into it;

FIG. 10 is a view partly in cross-section of the closure 34 in FIG. 6 and a pipetting needle 101 inserted through it.

Figure 1:
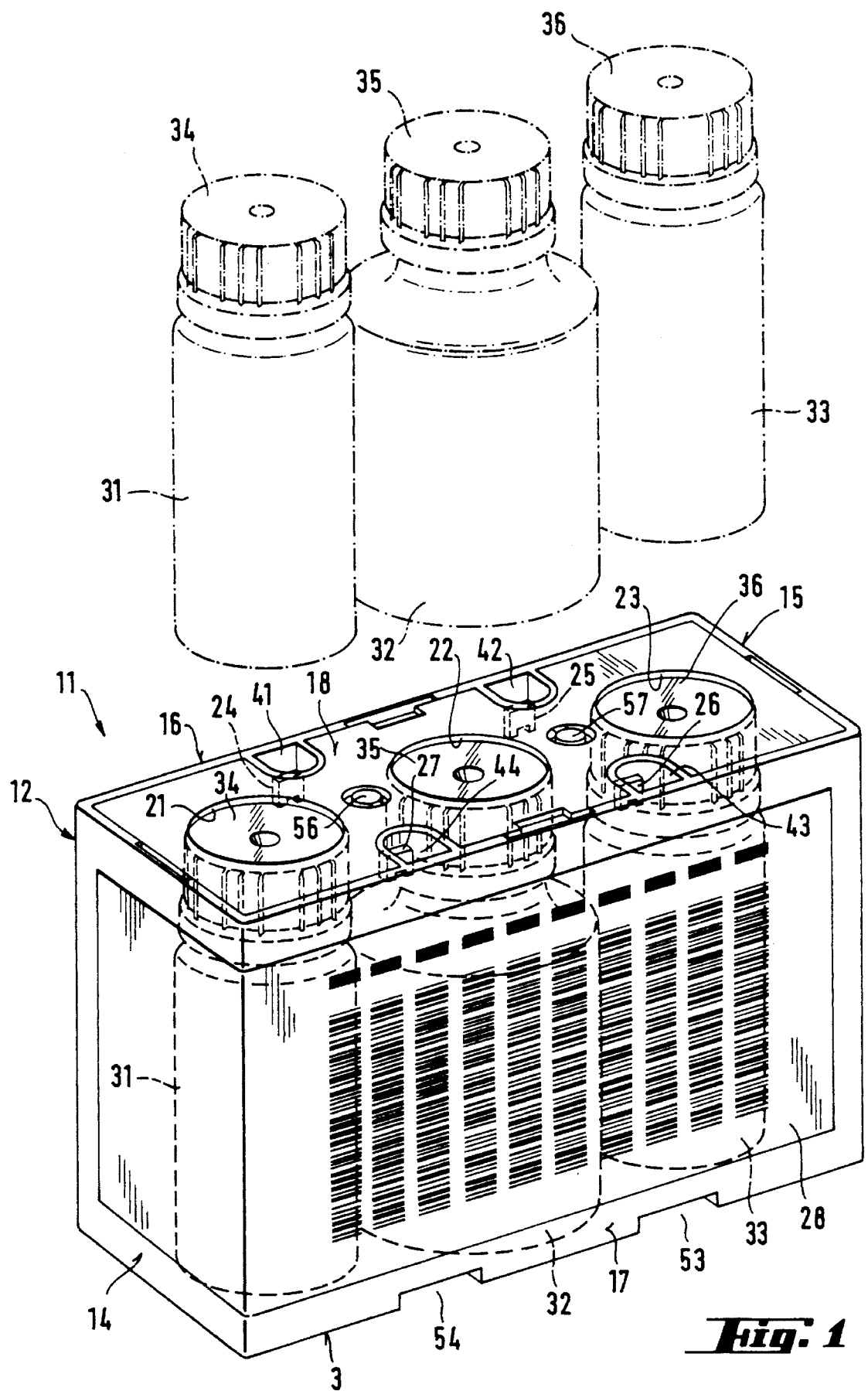
FIG. 1 is a perspective view of a reagent kit 11 according to the invention.

As FIG. 1 shows, a reagent kit 11 according to the invention substantially comprises a cuboid casing 12 and containers 31, 32, 33 disposed in the casing 12. The casing 12, which is made of suitable plastics such as polystyrene, has a bottom 13 (see FIG. 4), side walls 14, 15, 16, 17 and a removable lid 18. The lid 18 has openings 21, 22, 23 through which the contents of the reagent containers 31, 32, 33 are accessible for automatic pipetting operations. Each container 31, 32, 33 is closed by a closure 34, 35, 36, respectively, which closure can be perforated by a needle 101 (FIG. 10) of the pipetting device of an analytical apparatus (FIG. 11) but re-closes and seals after the needle has been removed. Closures 34, 35, 36 are preferably as described in the European patent application with publication No. 0 504 697, corresponding to U.S. application Ser. No. 07/848,766, filed Mar. 10, 1992, the disclosure of which is incorporated herein by reference.

Illustratively, the casing 12 can be equipped with the following combinations of reagent containers:

For a test with three components: a container holding 25 ml of a reagent R1, a container holding 12.5 ml of a reagent R2 and a container holding 12.5 ml of a reference serum.

For a test with two components: a container holding 25 ml of a reagent R1, a container holding 12.5 ml of a reagent R1 and a container holding 12.5 ml of a reference serum.

For a test with one component: a container holding 25 ml of a reagent R1 and one or two containers holding 12.5 ml of reagent R1.

The reagent containers 31, 32, 33 can be made of plastic or glass or other conventional non-reactive materials used with in vitro diagnostic analysis.

The top part of the casing 12 has webs 24, 25, 26, 27 for gripping by a gripper 66 (FIG. 11) belonging to a conveyor of an analytical apparatus.

As seen in FIG. 1, one of the side walls of the casing, (e.g. side wall 17) can also bear a machine-readable label 28.

Figure 2:
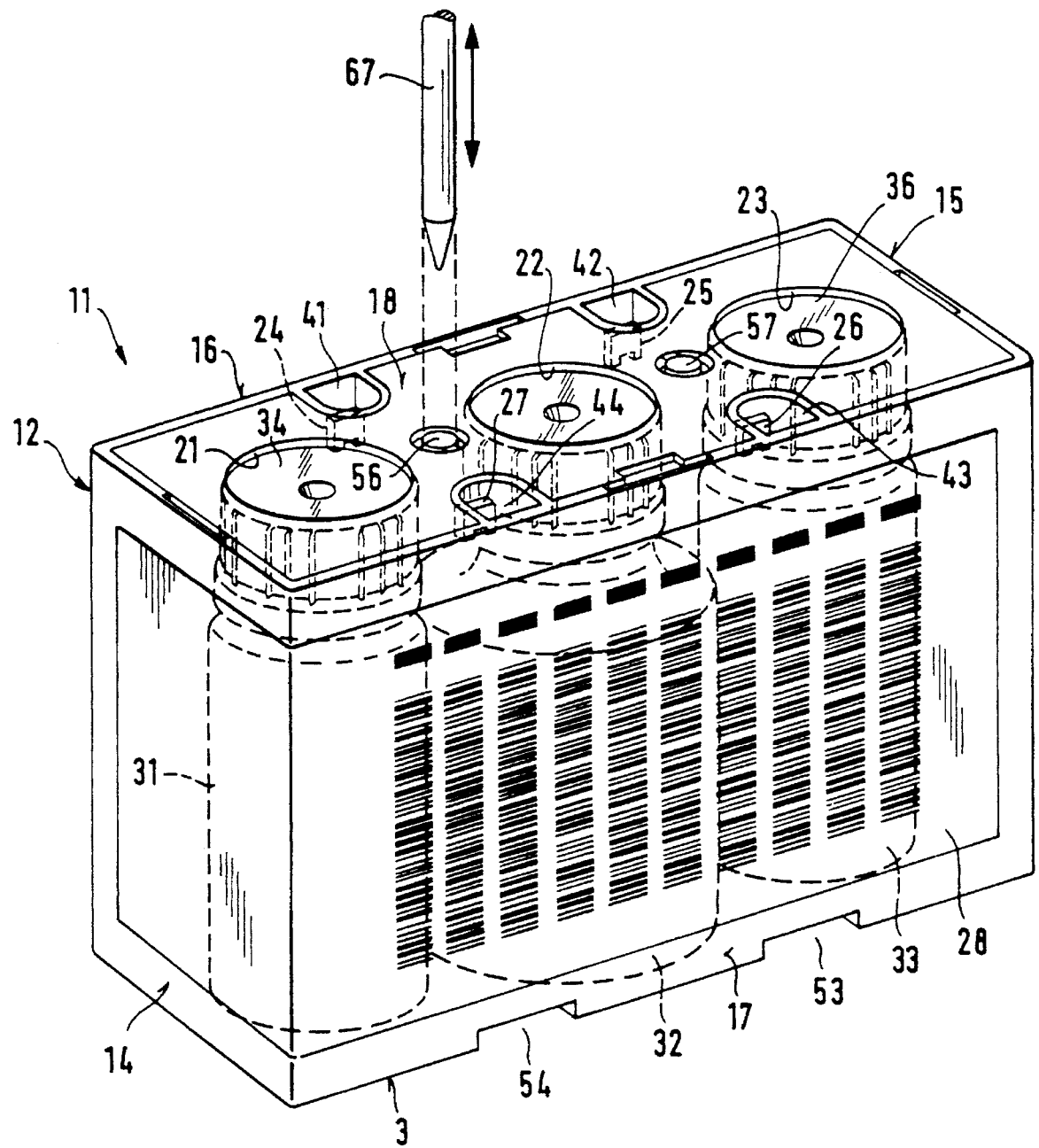
FIG. 2 shows a reagent kit 11 according to FIG. 1 and a spike 67 for checking or opening the pre-punched place 56 on a lid, 18 of the reagent kit 11.

As FIGS. 1 and 2 show, the lid 18 has pre-punched places 56 and 57 (e.g., ring with perforations) which can be opened by insertion of a spike 67.

Figure 3:
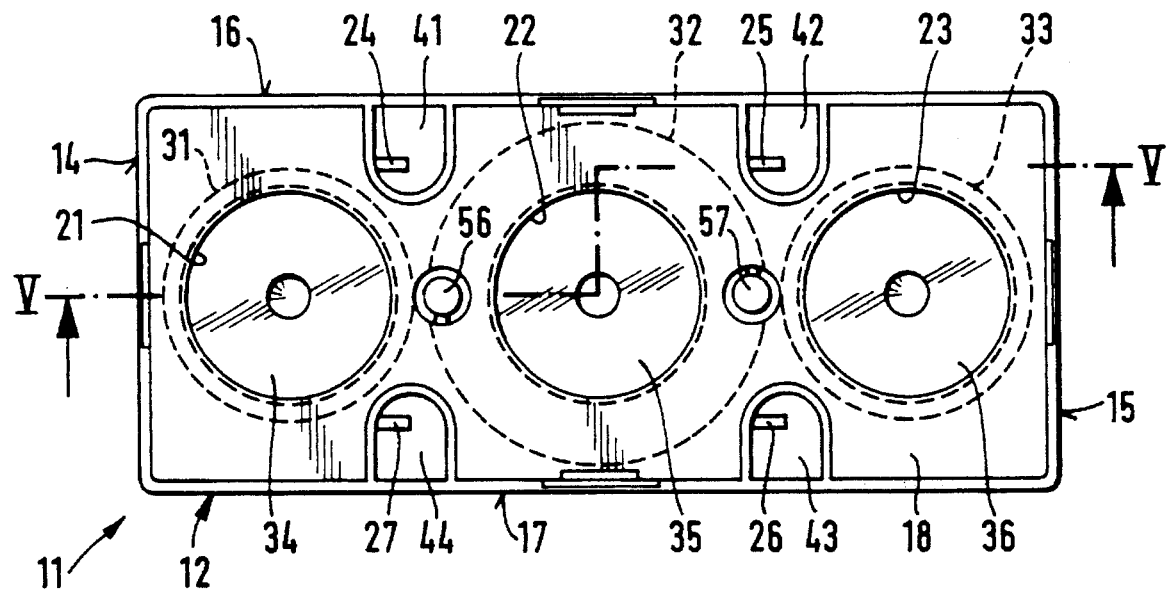
FIGS. 3 and 4 respectively are top and bottom views of the reagent kit 11 in FIG. 1.
Figure 4:
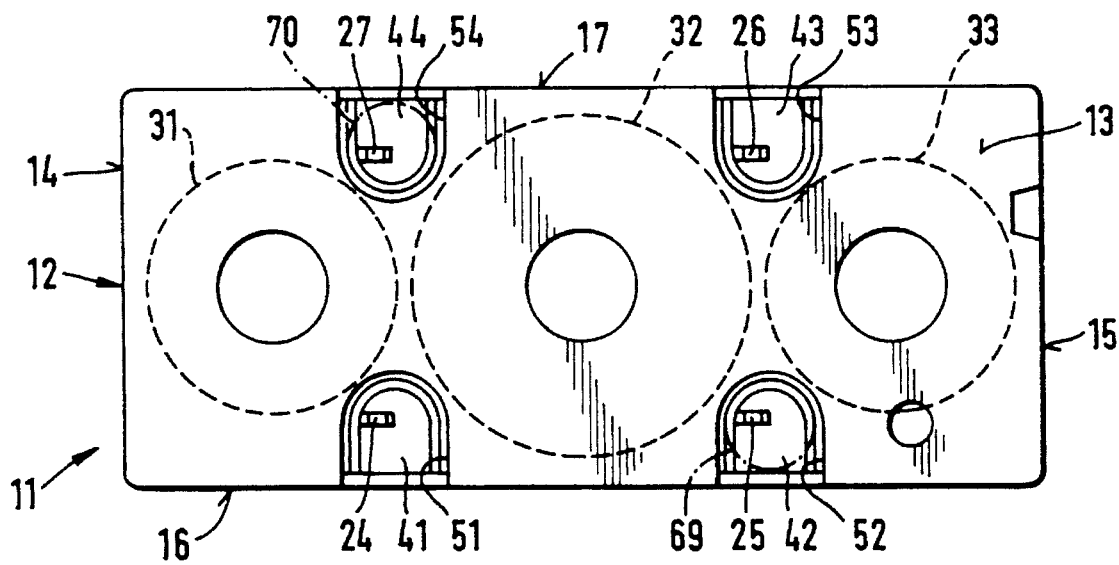
Figure 5:
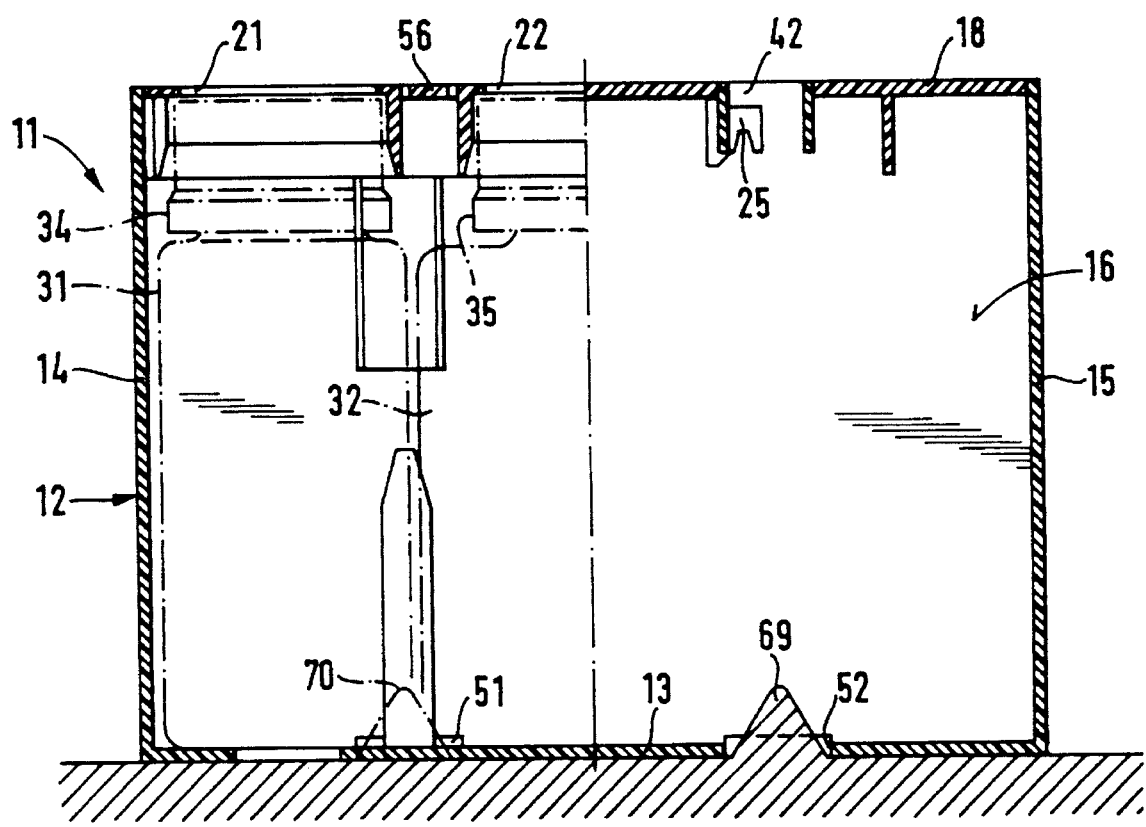
FIG. 5 is a front cross-sectional view through the reagent kit 11 in FIG. 1 taken along line V—V of FIG. 3.

As FIGS. 3 to 5 show, the bottom 13 and the lid 18 of casing 12 have openings 41–44 and corresponding openings 51–54 facing each other for circulating air through the interior of the casing 12 and the containers 31, 32, 33 therein. This is a means of uniformly cooling the containers in the reagent kit (see reference hereinafter to cooling; carrier plate 62 in FIG. 11).

Figure 6:
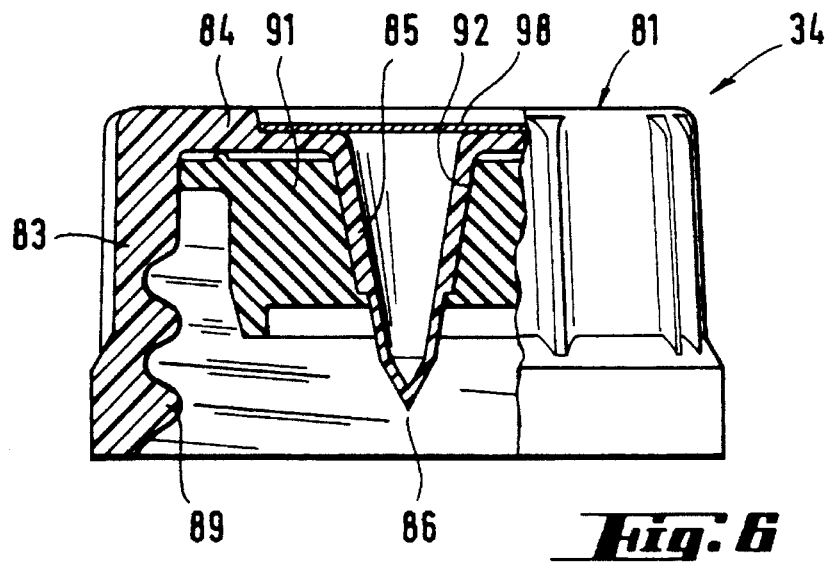
FIG. 6 is a view partly in cross-section of one of closures 34–35 in FIG. 5.
Figure 7:
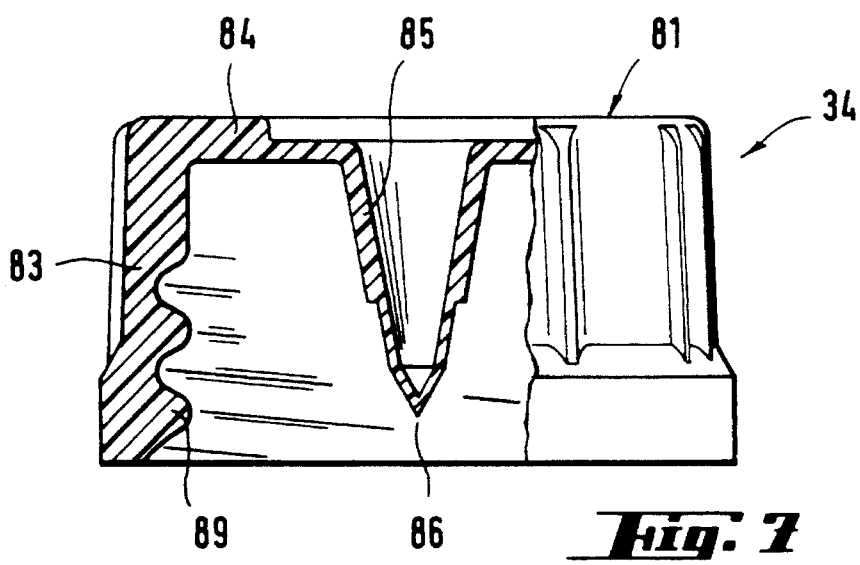
FIG. 7 is a view partly in cross-section of lid 81 in FIG. 6.
Figure 8:
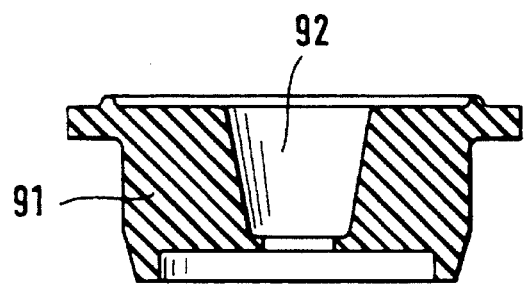
FIG. 8 is a cross-section of stopper 91 in FIG. 6.

The closures 34–36 in FIG. 1 have the same configuration and are constructed similarly. The construction of closure 34 will now be described with reference to FIGS. 6–8. As shown in FIGS. 6–8, the closure 34 substantially comprises a lid 81 and a stopper 91 for insertion as a seal between the lid 81 and the container.

The lid 81 in FIG. 7 is moulded in one piece from plastic. It has a cylindrical side wall 83 and an annular upper wall 84 which is adjacent the side wall. Upper wall 84 has a recessed inner circular section which is centered along the axis of symmetry and merges into a conical wall 85 which extends inwards from the inner circular section of the upper wall and ends in a tip 86 situated on the axis of symmetry of the cylindrical wall. The tip is configured adapted to be perforated (e.g. by the needle of an automatic pipetting device). A first part of the conical wall 85 adjacent the upper wall 85 is at an angle of about 10° to the axis of symmetry of the cylindrical side wall 83. The conical wall 85 has a second part which forms the tip 86 of the conical wall and is at an angle of about 30° to the axis of symmetry of the cylindrical side wall 83.

The lid 81 is a screw cap having side wall 83 with an inner thread 89 which corresponds to an outer thread in the neck of the reagent container (not shown) closed by the closure 34.

Access to the conical wall 85 is preferably sealed by a metal sealing foil 98.

FIG. 8 shows a stopper 91 having a central passage 92, the shape of which is configured and dismensioned to match the outer surface of the conical wall 85 of the lid, so that when the container is closed and sealed by the stopper 91 and lid 81. The outer surface of the conical wall 85 abuts in sealing-tight relationship against the inner wall of the passage 92 through the stopper 91.

Use of the closure 34 in FIG. 6 will now be described with reference to FIGS. 9 and 10.

As shown in FIG. 9, the tip 86 of the conical wall 85 is perforated by the point of a spike 90, which has cutting blades 87 and 88. In addition to the central opening formed by spike 90, the sharp bottom edges of the blades 87, 88 cut into and through the bottom part of the conical wall 85 to form side slots 94 and 95 (FIG. 10). After the spike 90 has been removed, the conical wall 85 defines slots 94 and 95, which are used for ventilation during pipetting operations.

As shown in FIG. 10, a pipetting needle 101 can then be inserted into the reagent container 31 (not shown) through the central opening left by the spike 90 at the tip 86 of the conical wall 85. The pipetting needle can thus be used to withdraw a given volume of liquid reagent from the container.

Figure 11:
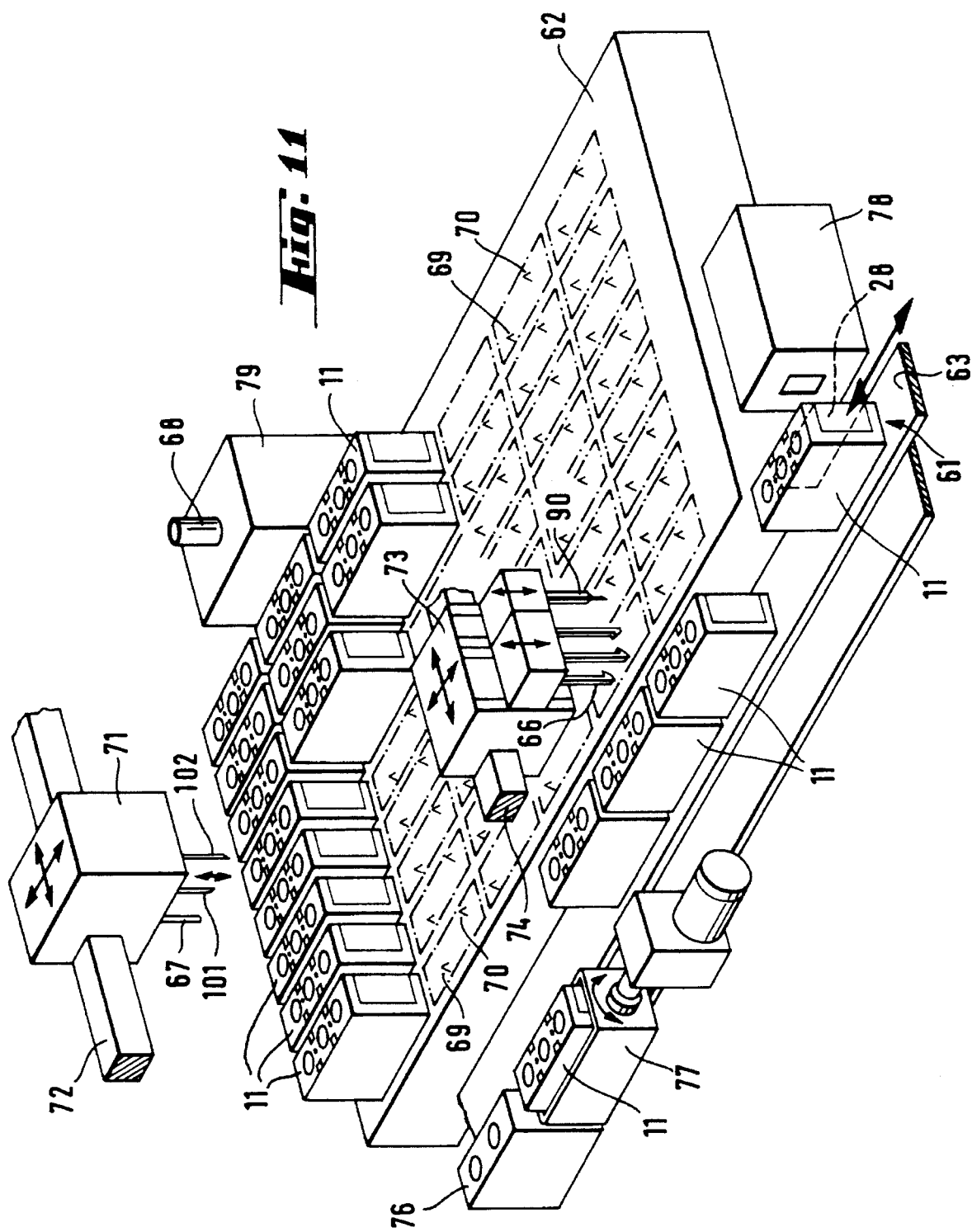
FIG. 11 is a perspective view of an analytical apparatus according to the invention.

As described hereinafter with reference to FIG. 11, an automatic analytical apparatus according to the invention is adapted to hold a number of the above-described reagent kits 11. As shown in FIG. 11, an analytical apparatus of this kind contains an input station 61 for inserting new reagent kits 11 into the apparatus, and an output station 61 for discharging used reagent kits 11 from the apparatus.

The analyzer also has a carrier plate 62 on which the reagent kits 11 received in the analytical apparatus are disposed in a predetermined matrix, projections 69, 70 being provided for exact positioning of the reagent kits onto carrier plate 62. There also is a conveyor (see e.g., 63, 73 and 66) for conveying the reagent kits 11 from the input station to the carrier plate 62 or from the carrier plate to the output station 61 and optionally to other positions inside the analytical apparatus, and an automatic pipetting device (see e.g., 71, 72) for carrying out pipetting operations as required in the analytical apparatus. These pipetting operations include removal of given volumes of reagent from reagent containers within reagent kits 11 and transfer of said volumes to reaction vessels, each of which contains a specimen for examination. Each reagent container is closed by a closure which can be perforated by the needle of the pipetting device (see FIGS. 9 and 10).

A central control device (not shown in FIG. 11) controls all the operations in the analytical apparatus.

The carrier plate 62 can be cooled by a coventional cooling device (e.g., fan, not shown). By this means, and as a result of the aforementioned circulation of air through the casing 12 of the reagent kits (see FIG. 3), the reagents contained therein are uniformly cooled.

In the embodiment in FIG. 11, the same location designated as symbol 61 is used as an input station and as an output or delivery station. In that case, the operator needs to be informed by a display showing the status of location 61. That is, the operator must know whether the station 61 is free for inserting reagent kits or whether it is occupied. Alternatively, there can be separate input and delivery stations.

In accordance with the preferred embodiment, up to five reagent kits simultaneously can be inserted at the input station 61. Used reagent kits are automatically returned to the delivery station, where they are discharged or removed from the apparatus.

As FIG. 11 shows, the analytical apparatus contains a reader 78 disposed at the input station 61 for reading machine-readable information. Illustratively, the information could be in the form of a bar code carried by a label 28 on the side 17 of the reagent kit 11 (see FIG. 11). The information on the label 28 is automatically read by the reader 78 when the reagent kit is inserted into the input station. The information carried in machine-readable form on the label contains identification of the test to be performed on the reagent kit, and parameters relating to the batch of reagents.

The conveyor for conveying the reagent kits 11 more particularly comprises a conveyor belt 63, which transports reagent kits 28 inserted at the input station 6 to the interior of the analyzer or back from there to the output station 61, and a gripper 66 guided by a carriage 73 conveying the pipetting needle (not shown) of an automatic pipetting device of the analytical apparatus. The gripper 66 cooperates with webs 24, 25, 26, 27 (see FIG. 1) to grip a reagent kit, e.g. from its position on carrier plate 62 or an belt 63. The carriage 73 carries the gripper 66 together with two pipetting needles (omitted for simplicity in FIG. 11), and for example, a spike 90 for acting on and penetration of wall 85 of the lid of a reagent container.

The carriage 73 and a rod 74 on which the carriage 73 moves belong to the conveyor of an automatic pipetting device in the analytical apparatus. The conveyor is used mainly for moving the pipetting needle in three directions at right angles to one another, to a number of pipetting positions.

In the preferred embodiment of FIG. 11, a second automatic pipetting device is provided and likewise contains a conveyor for moving pipetting needles 101, 102. The conveyor contains a carriage 71 and a rod 72 on which the carriage 71 moves. The carriage 71 carries the pipetting needles 101, 102 and a spike 67 which, as previously described with respect to FIG. 2, is used for broaching new reagent kits in the analytical apparatus or for determining the state of the reaction kits supplied to the analytical system.

The previously-mentioned pipetting operations are inter alia for removing given volumes of reagent from the containers 31, 32, 33 (not shown) contained in one of the reagent kits placed on the carrier plate 62 and for transferring them to predetermined reagent vessels 68 each holding a specimen for examination. During its entire period of use in the analytical apparatus, each reagent container 31, 32, 33 is closed by a stopper 34, 35 or 36 which can be perforated by the needles 101, 102 of the pipetting device (see FIGS. 1 and 8–10).

A preferred embodiment of the analytical apparatus as described in FIG. 11 contains means for checking whether each reagent kit 11 introduced into the analytical apparatus is intact. The checking device means substantially comprises the spike 67 shown in FIG. 11, the spike being carried by the carriage 71 of the needles 101, 102 and co-operating with a sensor arrangement (not shown). In order to check that a reagent kit 11 is intact, a suitable drive guides the spike 67 against one of the pre-punched places 56, 57 in the lid of the reagent kit 11 (see FIG. 1). If the spike 67 finds this place closed, it is taken as confirmation of the intactness of the reagent kit 11. The place is then opened by suitable pressure exerted by the spike, in order to broach the reagent kit. If on the other hand the spike finds that the punched place is open, this indicates that the reagent kit has already been broached and therefore should not be used again. In that case the conveyor will convey the reagent kit to the delivery station 61.

As FIG. 11 shows, the analytical apparatus comprises a processing station 77 in which a reagent kit disposed therein can be pivoted or rolled. If a reagent kit contains a reagent container holding a reagent in freeze-dried form the conveyor of reagent kits automatically brings such a kit to processing station 77 before first use of the kit. At its position on the carrier plate 62 the container is filled beforehand with a suitable amount of water by pipetting. Next, the reagent kit with the container is moved by the gripper 66, operated by the conveyor, from its position on the carrier plate 62 to the processing station 77. At station 77, the reagent kit 11 is pivoted for about 10 minutes so as to efficiently mix and completely dissolve the reagents requiring to be dissolved. All the reagents in a kit are dissolved simultaneously. After the reagents in kit 11 have been dissolved in the processing station 77, the kit is returned to its position on the carrier plate 62.

If required, certain reagent kits can periodically be re-mixed in the processing station 77 (e.g. once a day) via actuating means in the analytical apparatus.

After the freeze-dried reagents have been dissolved as described, the kit is broached as previously mentioned. Kits containing only liquid reagents and therefore not needing to be dissolved, will only be broached during the corresponding stage in the treatment of the reagent kits.

A station 76 for washing the pipetting needles is disposed alongside the processing station 77.

During operation of the analytical apparatus, volumes of reagent are selectively taken from a kit 11 available on the carrier plate 62 and supplied to a reaction vessel 68 in a station 79 for processing mixtures of specimen and reagent.

The invention has been described with reference to specifically preferred embodiments. Additional embodiments within the skill of an artisan are contemplated and intended to be included within the inventive concept.

We claim:

1. A reagent kit adapted for use in an analyzer having a pipetting device, the reagent kit comprising (i) a casing having a bottom, side walls and a removable lid and (ii) at least one individually removable reagent container, wherein:

(a) the bottom, side walls, and lid are configured and dimensioned to enclose and keep therewithin the at least one reagent container;

(b) the lid defines at least one opening which is positioned such that the at least one reagent container is accessible for automatic pipetting operations by a pipetting device; and (c) the lid defines at least one other opening which is of sufficient dimension for circulating air through the interior of the casing and around the at least one reagent container, within which opening is positioned a protruding surface configured and dimensioned to be gripped by a gripper means of the analyzer for automatic transport of the reagent kit from a first position to a second position.

2. The reagent kit of claim 1, wherein the reagent container is closed by a closure, said closure having a means for perforation by a needle of the pipetting device.

3. The reagent kit of claim 1, wherein one side wall of the casing includes a machine-readable label.

4. The reagent kit of claim 1, wherein the lid has at least one portion that is perforated.

5. The reagent kit of claim 1, wherein the bottom and the lid of the casing define openings of sufficient dimension for circulating air through the interior of the casing and around the at least one reagent container, each such opening of the bottom facing a corresponding opening of the lid.

\* \* \* \* \*